US008871947B2

United States Patent
Wang et al.

(10) Patent No.: US 8,871,947 B2
(45) Date of Patent: Oct. 28, 2014

(54) PREPARATION OF ALKYL 3-DIFLUORO-METHYL-1-METHYL-1H-PYRAZOLE-4-CARBOXYLIC ACID ESTER

(71) Applicant: KingChem LLC, Allendale Park, NJ (US)

(72) Inventors: Zheqing Wang, Union City, CA (US); Angang Wang, Dalian (CN)

(73) Assignee: KingChem LLC, Allendale Park, NJ (US)

( * ) Notice: Subject to any disclaimer, the term of this patent is extended or adjusted under 35 U.S.C. 154(b) by 0 days.

(21) Appl. No.: 14/145,073

(22) Filed: Dec. 31, 2013

(65) Prior Publication Data

US 2014/0221669 A1    Aug. 7, 2014

Related U.S. Application Data

(60) Provisional application No. 61/849,871, filed on Feb. 4, 2013.

(51) Int. Cl.
| C07C 67/343 | (2006.01) |
| C07D 231/14 | (2006.01) |
| C07C 67/313 | (2006.01) |
| C07C 67/36  | (2006.01) |

(52) U.S. Cl.
CPC ............ C07D 231/14 (2013.01); C07C 67/313 (2013.01); C07C 67/36 (2013.01)
USPC ........................................ 548/374.1; 560/174

(58) Field of Classification Search
None
See application file for complete search history.

(56) References Cited

U.S. PATENT DOCUMENTS

| 4,647,689 A | 3/1987 | Micinski |
| 4,883,904 A | 11/1989 | Amiet et al. |
| 5,093,347 A | 3/1992 | Graneto et al. |
| 5,498,624 A | 3/1996 | McLoughlin et al. |
| 7,358,387 B2 | 4/2008 | Lantzsch et al. |
| 7,678,924 B2 | 3/2010 | Walter et al. |
| 7,863,460 B2 | 1/2011 | Aihara et al. |
| 7,939,673 B2 | 5/2011 | Pazenok et al. |
| 8,115,012 B2 | 2/2012 | Sukopp et al. |
| 8,207,354 B2 * | 6/2012 | Maywald et al. .......... 548/374.1 |
| 8,258,335 B2 | 9/2012 | Pazenok et al. |
| 8,269,020 B2 | 9/2012 | Bowden et al. |
| 8,314,233 B2 | 11/2012 | Zierke et al. |
| 8,344,157 B2 | 1/2013 | Wolf et al. |
| 8,350,053 B2 | 1/2013 | Pazenok et al. |
| 2006/0149091 A1 | 7/2006 | Gallenkamp et al. |
| 2008/0004465 A1 | 1/2008 | Walter et al. |
| 2009/0221588 A1 | 9/2009 | Haas et al. |
| 2011/0004002 A1 | 1/2011 | Maywald et al. |
| 2011/0009642 A1 | 1/2011 | Pazenok |
| 2011/0040096 A1 | 2/2011 | Zierke et al. |
| 2011/0172436 A1 | 7/2011 | Wolf et al. |
| 2012/0065407 A1 | 3/2012 | McDougald et al. |
| 2012/0302608 A1 | 11/2012 | Hughes et al. |
| 2013/0012722 A1 | 1/2013 | Zumpe et al. |
| 2013/0123510 A1 | 5/2013 | Braun et al. |
| 2013/0197239 A1 | 8/2013 | Pazenok et al. |
| 2013/0274481 A1 | 10/2013 | Wang et al. |
| 2014/0107347 A1 | 4/2014 | Okamoto et al. |

FOREIGN PATENT DOCUMENTS

| CN | 102702104 A | 10/2011 |
| CN | 102766096 A | 7/2012 |
| CN | 102731402 A | 10/2012 |
| JP | 2013006778 A | 1/2013 |
| JP | 2013006779 A | 1/2013 |
| JP | 2013006780 A | 1/2013 |
| JP | 2013006782 A | 1/2013 |
| WO | 2011113788 A1 | 9/2011 |
| WO | 2012025469 A1 | 3/2012 |

OTHER PUBLICATIONS

Henne et al., "The Alkaline Condensation of Fluorinated Esters with Esters and Ketones" J. Am. Chem. Soc. vol. 69, (1947), pp. 1819-1820.
Mcbee et al., "The Preparation and Reactions of Fluorine-Containing Acetoacetic Esters" J. Am. Chem. Soc. vol. 75, (1953) pp. 3152-3153.
Search Report of the International Searching Authority for International Patent Application No. PCT/US2014/010634; International Filing Date: Jan. 8, 2014; Date of Mailing: Feb. 27, 2014; 4 Pages.
Written Opinion of the International Searching Authority for International Patent Application No. PCT/US2014/010634; International Filing Date: Jan. 8, 2014; 5 Pages.

* cited by examiner

*Primary Examiner* — Kamal Saeed
(74) *Attorney, Agent, or Firm* — Cantor Colburn LLP

(57) ABSTRACT

The present disclosure provides a novel and economically advantageous process for preparation of compounds of Formula I, such as alkyl 3-difluoromethyl-1-methyl-1H-pyrazole-4-carboxylic acid ester. The process includes acidification of the sodium enolate of alkyl difluoroacetoacetate by carbonic acid generated in situ by reacting carbon dioxide with water. The disclosure also includes promoting the ring closure reaction in which alkyl 2-alkomethylene-4,4-difluoro-3-oxobutyrate is reacted with methylhydrazine in two phase system with a weak base such as $Na_2CO_3$ or $K_2CO_3$.

17 Claims, No Drawings

PREPARATION OF ALKYL 3-DIFLUORO-METHYL-1-METHYL-1H-PYRAZOLE-4-CARBOXYLIC ACID ESTER

CROSS REFERENCE TO RELATED APPLICATION

The application claims priority from U.S. Provisional Appl. No. 61/849,871 filed Feb. 4, 2013, which is hereby incorporated by reference in its entirety.

BACKGROUND

The disclosure provides a novel process for the production of alkyl 3-difluoromethyl-1-methyl-1H-pyrazole-4-carboxylic acid ester of Formula I, a precursor used for preparing 3-difluoromethyl-1-methyl-1H-pyrazole-4-carboxylic acid of Formula II.

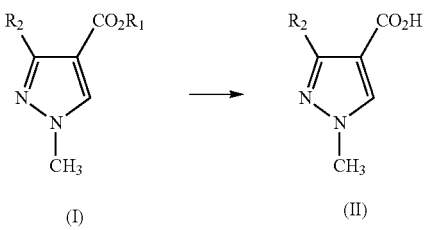

The acid of Formula II is used for produce fungicides. Annual productions of fungicides exceeds more than 30,000 metric tons. Any improvement in cost efficiency or waste reduction has large economic and environmental benefits.

The preparative routes for Formula I reported to date in the patent and non-patent literature all include reacting an alkyl haloethylacetate, such as an alkyl difluoroethylacetate of Formula III-A with alkyl acetate of Formula IV-A via Claisen ester condensation to provide the enolate salt of difluoroacetoacetate of Formula V-A.

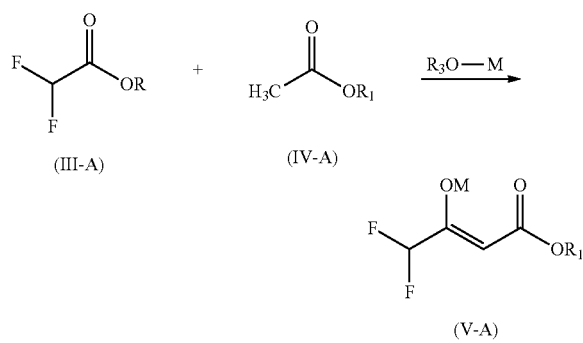

The enolate salt of Formula V-A is then acidified to release the free alkyl difluoroacetoacetate of Formula VI-A.

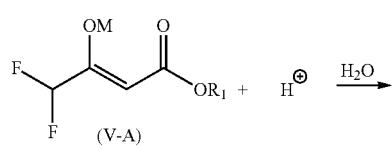

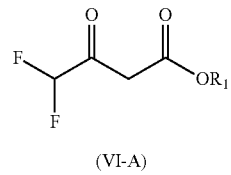

The alkyl difluoroacetoacetate of Formula VI-A is then coupled with trialkyl orthoformate in the presence of excess acetic anhydride to provide an intermediate, alkyl 2-alkomethylene-4,4-difluoro-3-oxobutyrate of Formula VII.

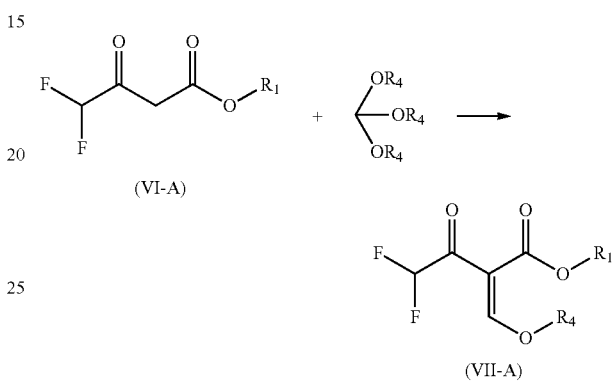

The intermediate of Formula VII-A is then reacted with methylhydrazine hydrate to provide 3-difluoromethyl-1-methyl-1H-pyrazole-4-carboxylic acid ester of Formula I-A, which can be hydrolyzed to give the acid of Formula II-A. Formula I-A is a particular form of generic Formula I in which $R_2$ is $CF_2$.

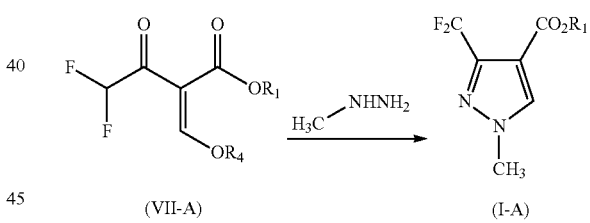

Much effort has been made to improve the reaction conditions and/or work up methods in order to achieve higher yields or greater purity and to reduce chemical waste.

Typically, the work up process of the Claisen condensation has included adding an acidic aqueous solution, such as HCl, HBr, $H_2SO_4$, $H_3PO_4$, or acetic acid aqueous solution to neutralize the basic salt of enolate of the ester. The released alkyl haloacetoacetate, typically difluoroacetoacetate, is used for next step after distillation.

WO 2009/106619 describes an improved method in which an acid, such as concentrated sulfuric acid, formic acid, acetic acid, oxalic acid, methanesulfonic acid or p-toluenesulfonic acid is added into the reaction mixture after the Claisen condensation in complete to acidify the basic enolate.

Alternatively, a gaseous acid, such as HCl-gas or HBr-gas is introduced into the reaction mixture accompanied by a small amount of water. The gas must be bubbled through the reaction mixture for several hours to release the free ester (Formula V, or more particularly Formula V-A or Formula V-B).

The resulting inorganic salt exists as a suspended solid, in the form of NaCl, NaBr, Na₂SO₄, sodium acetate, sodium methanesulfonate, or sodium formate, and is collected by filtration. The filtrate is used for next step.

The solid wastes produced in the existing procedures for producing a compound of Formula I are hazard and toxic. The accumulated amount from industrial production of Formula I can be up to ten thousand tons per year. Treating this amount of hazardous waste is a considerable manufacturing cost and inconvenience. Moreover, due to the corrosive nature of HCl-gas or HBr-gas the manufacturing facility must be corrosion resistant and must be fitted with corrosion resistant equipment.

WO 2011/113789 provided a minor additional improvement. After the Claisen condensation is completed without adding any water, excess HCl-gas is introduced. The HCl gas is bubbled through the reaction mixture for up to several hours. The formed inorganic solid is not removed. The whole suspended reaction mixture, including organic solvents and inorganic solids, is then transferred into another reactor for the next step. Transferring the viscous, crude reaction product is difficult.

Early literature and patents reported the pyrazole ring formation in a single solvent such as ethanol or water. The crude product required recrystallization for purification to provide light yellow solid, with a yield of about 60%. U.S. Pat. No. 7,863,460, U.S. Pat. No. 8,124,787, and JP 5232335 disclose similarly effective ring-closure methods. The methods are conducted in water and a water-immiscible organic solvent system in the presence of a base, which can produce a compound of Formula I with high regioselectivity for the desired isomer of Formula I, alkyl 5-difluoromethyl-1-methyl-1H-pyrazole-4-carboxylic acid ester. Formula-VIII, the undesired isomer is produced as a minor component.

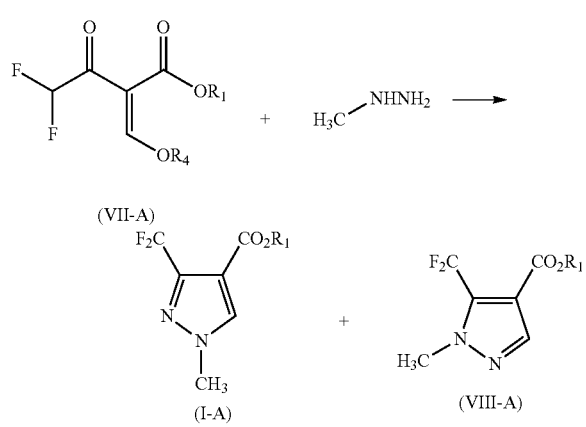

The base used for the ring closure reaction in the U.S. Pat. No. 7,863,460, U.S. Pat. No. 8,124,787, and JP 5232335 patents is selected from alkali metal hydroxides and alkali earth metal hydroxides. The amount of the base used is from 0.05 to 5.0 equivalents based on alkyl 2-alkoxymethylene-4,4-difluoro-3-oxobutyrate (Formula VII-A). When the ratio of base to compound of Formula VII-A reaches to 1:1 equivalents or higher the ester group has a tendency to be saponified to form the salt of Formula IX.

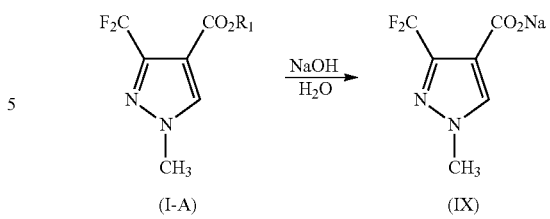

salt dissolves in the water phase and is taken off during two phase separation resulting in a loss of the product.

The above review of previously reported methods for preparing an alkyl 3-difluoromethyl-1-methyl-1H-pyrazole-4-carboxylic acid ester of Formula I demonstrates the need for an improved reaction work-up following the Claisen condensation. and a method for producing an alkyl 3-difluoromethyl-1-methyl-1H-pyrazole-4-carboxylic acid ester of Formula I without the use of strong acid to avoid the production of large amounts of hazardous waste and the difficulties of fitting a production facility for a corrosive manufacturing process. It is also desirable to provide a method for preparing a compound of Formula I in which the ring closure step is conducted with high yield and high regioselectivity.

SUMMARY OF THE INVENTION

The disclosure provides a process for preparing a compound Formula V by Claisen condensation. In the first step a haloalkylacetate of Formula III is reacted with an alkyl acetate of Formula IV to provide the enolate salt of Formula V

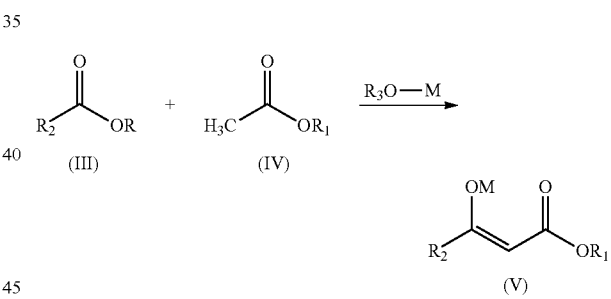

wherein
R is $C_1$-$C_6$ alkyl;
$R_1$ is $C_1$-$C_6$ alkyl; and
$R_2$ is $CF_2H$, $CFH_2$, $CF_3$, $CCl_2H$, $CClH_2$, or $CCl_3$;
and $R_3$ is methyl or ethyl.

The disclosure provides a process for producing a compound of Formula VI

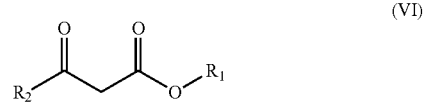

comprising adding carbon dioxide and water to a compound of Formula V to generate carbonic acid in situ and thereby acidifying the compound of Formula V to provide the compound of Formula VI

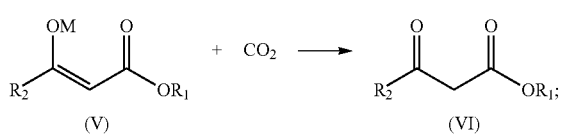

wherein
M is sodium, potassium, or lithium;
$R_1$ is $C_1$-$C_6$ alkyl; and
$R_2$ is $CF_2H$, $CFH_2$, $CF_3$, $CCl_2H$, $CClH_2$, or $CCl_3$.

In certain embodiments the process further comprises coupling the compound of Formula VI with a trialkyl orthoformate to provide a compound of Formula VII

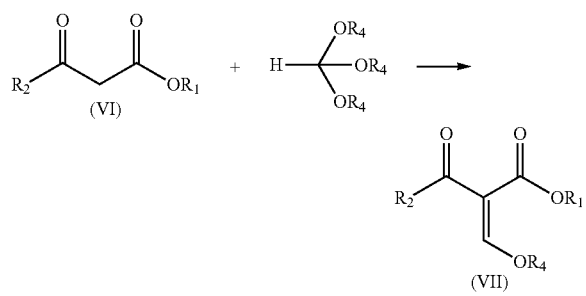

wherein $R_4$ is $C_1$-$C_6$alkyl.

The process may additionally comprise reacting the compound of Formula VII with methyl hydrazine hydrate ($H_3CNHNH_2 \cdot H_2O$) or methyl hydrazine to provide a compound of Formula I

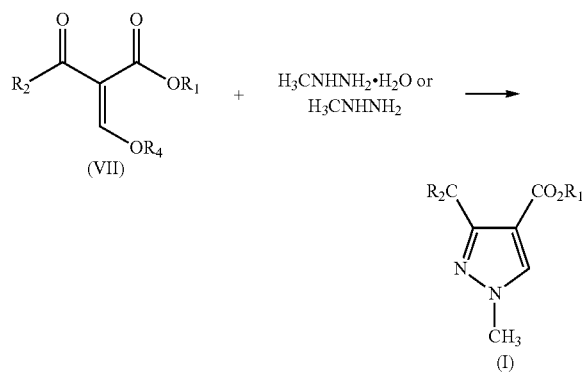

DETAILED DESCRIPTION

Carbon dioxide is a safe, low-cost, noncombustible gas. Carbon dioxide dissolves into water to form carbonic acid. Under atmospheric pressure, 171 ml of carbon dioxide dissolves in 100 ml of water at 0° C.; and 88 ml of carbon dioxide dissolves in 100 ml of water at 20° C. At atmospheric pressure carbon dioxide is converted to carbonic acid in water.

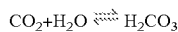

Under normal atmospheric pressure an aqueous saturated carbon dioxide solution maintains a pH of 5.7 at room temperature. If the pressure is increased to 2.5 atmospheres (the same pressure as in soda bottles) an aqueous saturated carbon dioxide solution maintains a pH of 3.7.

The inventors surprisingly found, after extensive research, that carbonic acid generated in situ by reacting carbon dioxide gas or solid carbon dioxide (dry ice) with water can effectively acidify the enolate salt of the alkyl haloacetoacetate ester. The reaction yield is comparable to that obtained when strong acids are used to acidify the enolate salt of the alkyl haloacetoacetate. The only by-product of acidification with in situ generated carbonic acid is sodium bicarbonate $NaHCO_3$, an environmentally harmless chemical that does not require special treatment. In contrast to the traditional methods for preparing compounds of Formula I which use strong acid and require specially equipped manufacturing facilities due to the corrosive nature of the process, the process disclosed here is chemically mild and does not require a specially equipped manufacturing facility or special corrosion resistant reaction apparatus.

Another object of the present invention is the provision of a novel method for the pyrazole ring-closure reaction that permits the production of a compound of Formula I with high yield and higher regioselectivity.

The inventors surprisingly found that the weak bases, such as sodium carbonate, potassium carbonate, sodium bicarbonate, or potassium bicarbonate in aqueous solution, can assist in closing the pyrazole ring more effectively than strong bases such as sodium hydroxide or potassium hydroxide. Weak bases have the added advantage of depressing the formation of the by-product, the undesired regioisomer of Formula VIII.

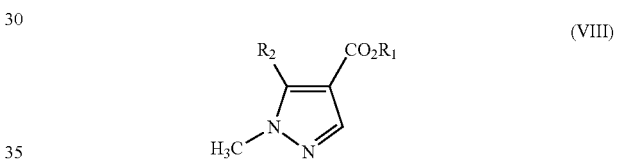

Moreover, weak bases such as sodium carbonate, potassium carbonate, sodium bicarbonate, and potassium bicarbonate are unable to saponify the ester group of Formula I, thereby preventing the loss of product due to saponification, and increasing the effective yield of the desired product of Formula I.

In a preferred embodiment the disclosure provides a method for preparing a compound of Formula I-A

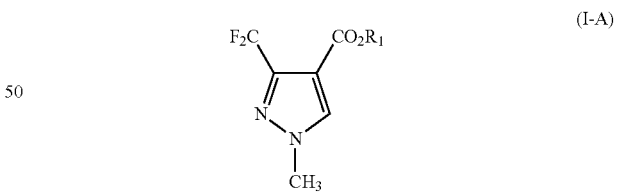

Within Formula I-A $R_1$ is $C_1$-$C_6$alkyl.

Step 1 is a Claisen reaction of an alkyl-difluoroacetate (Formula III-A),

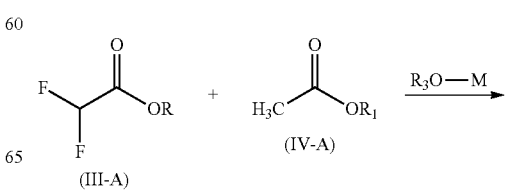

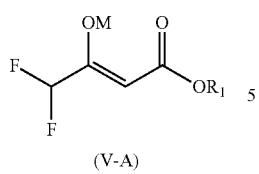

(V-A)

In Step 1 the variables, e.g. R, $R_1$, $R_3$, and M carry the following definitions.

R and $R_1$ are independently chosen from $C_1$-$C_6$alkyl; $R_3$ is methyl or ethyl, and M is Na or K.

In Step 2 the enolate salt of difluoroacetoacetate of Formula V-A is acidified by carbonic acid formed in situ by the introduction of carbon dioxide and water until the pH drops to between about 5 to 7. The reaction results in the release of the alkyl difluoroacetoacetate of Formula VI-A.

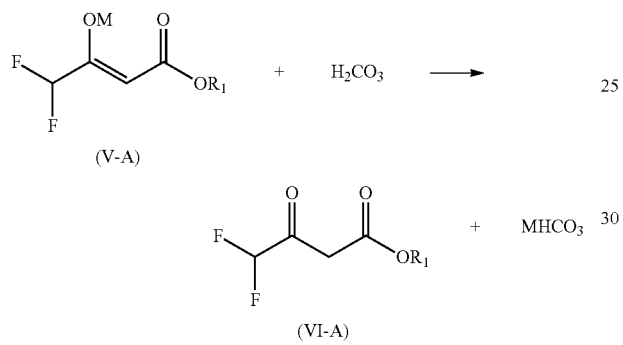

In Step 2 water is added to the reaction mixture followed by the introduction of carbon dioxide, for example gaseous carbon dioxide or solid carbon dioxide (dry ice). The pressure is kept in the range of about 0.1 kg/cm2-about 2 kg/cm2 for about 1 to about 3 hours. The pH of the mixture drops to about 5 to 7.

After the reaction has proceeded for the desired time, the pressure of carbon dioxide is reduced. Solid sodium bicarbonate forms and is removed by filtration. Sodium chloride is added to form a saturated aqueous solution. The two phases are separated. The aqueous phase is extracted with ethyl acetate. After vacuum evaporation the crude product of Formula VI-A is obtained.

The pure Formula VI-A is obtained after fractional distillation from the crude product with a yield range of 75 to 80%.

In Step 3 the purified alkyl difluoroacetoacetate of Formula VI-A is coupled with trialkyl orthoformate. The reaction is conducted in acetic anhydride to provide alkyl 2-alkomethylene-4,4-difluoro-3-oxobutyrate of Formula VII-A.

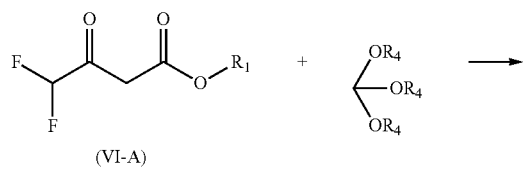

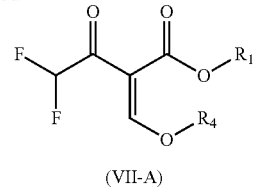

(VII-A)

$R_4$ is methyl or ethyl.

The ring-closing reaction (Step 4) to form the pyrazole ring is performed in a two phase system with assistance of a weak base such as sodium carbonate, potassium carbonate, sodium bicarbonate, or potassium bicarbonate.

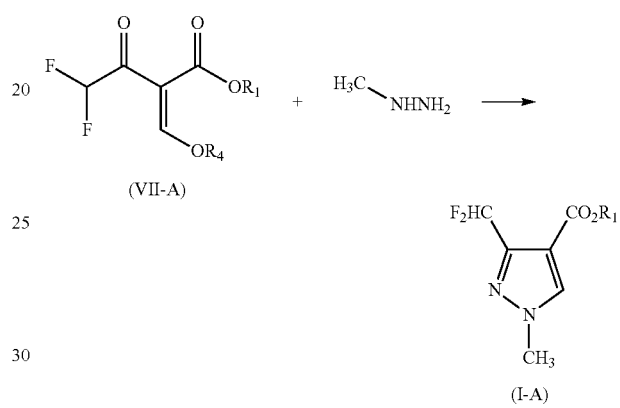

The sodium/potassium carbonate and methylhydrazine dissolve in water to form a solution. The solution is cooled to about −20° C. to about 5° C., or more preferably about −10° C. to about 0° C. The crude product of Formula VII-A, alkyl 2-alkomethylene-4,4-difluoro-3-oxobutyrate, dissolves in a water-immiscible organic solvent, such as toluene and xylene, and then is slowly added to the aqueous phase at the same temperature. The reaction is complete in about 1 to about 3 hours with effective stirring. The organic phase is separated and concentrated under vacuum. The residual solid is then dissolved into a mixed solvent system consisting of toluene and petroleum ether after heating. The product of Formula I-A is obtained with high purity (99.90%) which slowly precipitates out of solution and is collected by filtration.

The disclosure includes embodiments in which Formula I is purified in situ by precipitation from a solvent mixture. In certain embodiments the solvent mixture is selected from the group consisting of toluene/petroleum ether, toluene/hexane, toluene/pentane, toluene/heptane, toluene/cyclohexane, toluene/ethyl acetate, toluene/isopropylacetate, and toluene/butyl acetate.

In another embodiment the carbon dioxide added to the enolate salt of the haloacetoacetate (Formula V) is added to the water as gaseous carbon dioxide or solid carbon dioxide (dry ice) and thereby generates carbonic acid in situ. In this embodiment the pressure of carbon dioxide may be from about 0.1 kg/cm$^2$ to about 5 kg/cm$^2$.

In an embodiment the reaction of Formula VII with methyl hydrazine hydrate ($H_3CNHNH_2 \cdot H_2O$) or methyl hydrazine is conducted in the presence of a weak base.

In certain embodiments the weak base is selected from a carbonate salt or a bicarbonate salt or a combination thereof. The carbonate salt may be $Na_2CO_3$, $K_2CO_3$, $Li_2CO_3$, $CaCO_3$, or MgCO$_3$ or a combination of any of the foregoing. The bicarbonate salt may be NaHCO$_3$, KHCO$_3$, or LiHCO$_3$, or a combination of any of the foregoing.

The reaction of Formula VII with methyl hydrazine hydrate (H$_3$CNHNH$_2$·H$_2$O) or methyl hydrazine may be conducted in a two phase solution consisting of water and a water-immiscible organic solvent. The water-immiscible organic solvent may be toluene, xylene, pentane, hexane, heptane, cyclohexane, or methyl tertiary butyl ethyl (MTBE), or a combination of any of the foregoing.

The reaction of Formula VII with methyl hydrazine hydrate (H$_3$CNHNH$_2$·H$_2$O) or methyl hydrazine may be conducted at a temperature of from about −20° C. to about 20° C., or preferably from about −10° C. to about 10° C.

In certain of the above embodiments it is preferred that R and R$_1$ are selected from C$_1$-C$_3$alkyl, or the R and R$_1$ are independently methyl or ethyl, or that R and R$_1$ are ethyl. In certain of the above embodiments it is preferred that R$_2$ is CF$_2$H or CF$_3$, or more preferably that R$_3$ is ethyl. In certain of the above embodiments it is preferred that M is sodium. In certain of the above embodiments it is preferred that R$_4$ is ethyl.

Any of the above embodiments may be combined so long as a compound of Formula I results. Such combinations are contemplated as within the scope of the disclosure.

Compounds are described using standard nomenclature. Unless defined otherwise, all technical and scientific terms used herein have the same meaning as is commonly understood by one of skill in the art to which this invention belongs.

The term "Formula I" encompasses all compounds that satisfy Formula I, including any enantiomers, racemates and stereoisomers, and so forth, of such compounds. "Formula I" includes all subgeneric groups of Formula I, such as Formula I-A and Formula I-B. Formula I encompasses such compounds of Formula I in which R$_1$ or R$_2$ carries a particular definition, unless clearly contraindicated by the context in which the term "Formula I" is used. Formula I includes both the generic formula in which R$_2$ is CF$_2$H, CFH$_2$, CF$_3$, CCl$_2$H, CClH$_2$, or CCl$_3$ and the preferred form in which R$_2$ is CF$_2$H. Similarly, Formula III includes Formula III-A and Formula III-B, Formula IV, includes Formula IV-A and Formula IV-B and so forth.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Compounds of Formula I include all compounds of Formula I having isotopic substitutions at any position. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C.

"Alkyl" is a branched or straight chain saturated aliphatic hydrocarbon group, having the specified number of carbon atoms, generally from 1 to about 12 carbon atoms. The term C$_1$-C$_6$alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. C$_1$-C$_6$alkyl, C$_1$-C$_4$alkyl, and C$_1$-C$_2$alkyl. Examples of alkyl include, but are not limited to, methyl, ethyl, n-propyl, isopropyl, n-butyl, 3-methylbutyl, t-butyl, n-pentyl, and sec-pentyl.

The following examples further illustrate the specific aspects of the present process, and are not intended to limit the scope thereof in any respect.

EXAMPLES

Example 1

Preparation of Sodium Enolate of Ethyl 2,2-Difluoroacetoacetate (Formula V-B)

The sodium enolate of ethyl 2,2-difluoroacetoacetate (Formula V-B) is prepared from ethyl acetate and ethyl 2,2-difluoroacetate.

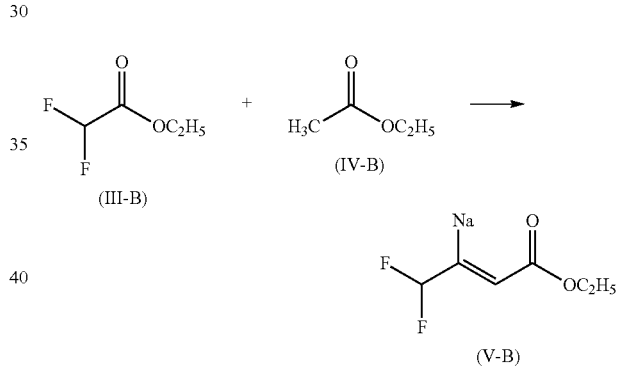

Ethyl acetate (176.2 g, 2.0 mol) is placed into flask under nitrogen atmosphere and cooled to 10° C. to 20° C. Sodium ethoxide (71.4 g, 1.05 mol) is added portion-wise into flask with stirring. The addition is exothermic. Ethyl 2,2-difluoroacetate (124.1 g, 1.0 mol) is charged under nitrogen. The temperature is raised to 60° C. to 65° C. and kept at that temperature for 2 hours. GC analysis indicates a conversion rate>98.0%.

Example 2

Preparation of Ethyl 2,2-Difluoroacetoacetate (Formula VI-B)

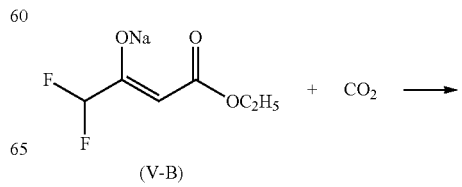

-continued

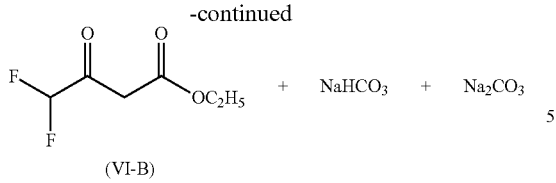

(VI-B)

Method-A (Using Carbon Dioxide Gas):

The reaction mixture containing sodium enolate of ethyl 2,2-difluoroacetoacetate (Formula V-B) is cooled to below 15° C. Water (371 g) is added to the cooled reaction mixture. Carbon dioxide gas is introduced to generate carbonic acid in situ. The pressure of the carbon dioxide is kept around 1 kg/cm2 for 1-2 hours. The pressure is then released, and the precipitated solid (sodium bicarbonate and small amount of sodium carbonate) is filtered off. Solid sodium chloride is added to filtrate to provide a saturated aqueous solution. The two phases are separated. The aqueous phase is extracted with ethyl acetate. The combined organic phases are evaporated to give the crude product of Formula VI-B (137.9 g, yield=83%). The crude product is then purified by fractional distillation to give the pure product (127.9 g, Y=77%).

Method B (Using Solid Carbon Dioxide):

Water (371 g) is added to the reaction mixture of sodium enolate of ethyl 2,2-difluoroacetoacetate (Formula V-B). Dry ice (solid carbon dioxide, 130 g) is added with slow stirring. After addition the reactor is sealed and then slowly warmed by running water in the reactor jacket. The temperature is kept around 20° C. for 2-3 hours. The carbon dioxide gas is released and the precipitated sodium bicarbonate is filtered off The work up procedure is the same as described for Method A. Alternatively, the crude product (Formula VI-B) can be directly used in next step without fractional distillation. The crude product yield is 141 g (84.9%).

Example 3

Preparation of Ethyl 2-Ethoxymethylene-4,4-Difluoro-3-Oxobutyrate (Formula VII-B)

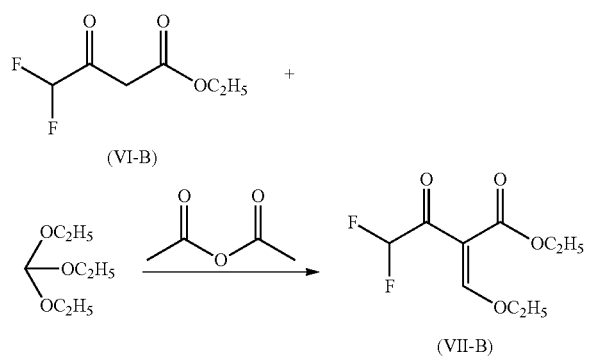

Acetic anhydride (3.6 moles) is heated to 100 to 105° C., to which a mixture of crude ethyl difluoroacetoacetate (~0.96 moles) and triethyl orthoformate (1.8 moles) is added drop-wise. The reaction mixture is kept at 100 to 105° C. for 6 hours. The reaction mixture is cooled to 60 to 70° C. and then concentrated under vacuum to remove excessive acetic anhydride, triethyl orthoformate, and generated ethyl acetate. A pale brown liquid is obtained.

Example 4

Preparation of Ethyl 3-Difluoromethyl-1-Methyl-1H-Pyrazole-4-Carboxylic Acid Ester (Formula I-b)

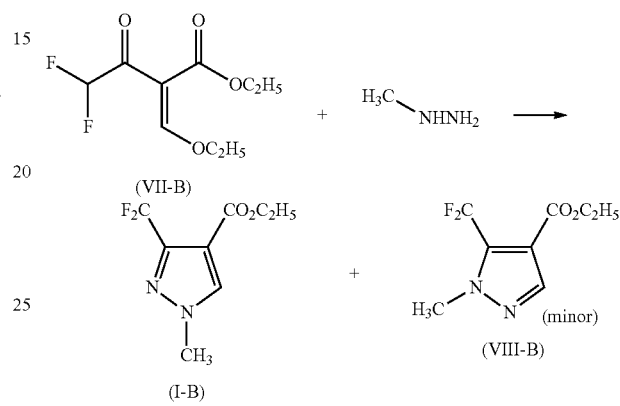

Potassium carbonate (237 g, 1.72 mol) and 40% methylhydrazine aqueous solution (565 g, 4.91 mol) are dissolved in water (2134 g) to make a solution. The solution is mixed with toluene (2292 g) and cooled to between −10° C. and −5° C. Ethyl 2-ethoxymethylene-4,4-difluoro-3-oxobutyrate of Formula VII-B (1146 g, 4.91 mol) dissolves in toluene (1146 g), which is then added drop-wise into the two phase methylhydrazine solution while maintaining effective agitation in the same temperature range. The reaction is finished within 1-2 hours after addition of Formula VII-B. (GC analysis indicates the content of ethyl 2-ethoxymethylene-4,4-difluoro-3-oxobutyrate of Formula-VII-B<0.2%). The reaction mixture is concentrated under vacuum. Toluene (757 g) and petroleum ether (b.p. 60° C. to 90° C.) (3028 g) are added to the residual solid. The mixture is heated to 50° C. to 55° C. to make a solution. The solution is cooled slowly to a range of 10° C. to 15° C. The product precipitates as a pale yellow crystal. (855 g, yield 83.8%). It has a high purity of 99.90% with only 0.05% of the regioisomer of Formula VIII-B.

We claim:

1. A process for—producing a compound of Formula VI

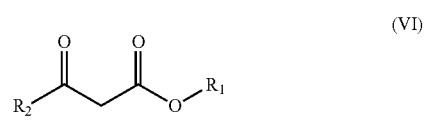

comprising adding carbon dioxide to a compound of Formula V in water to generate carbonic acid in situ and thereby acidifying the compound of Formula V to provide the compound of Formula VI

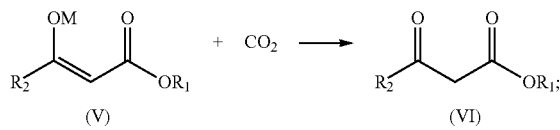

(V)   (VI)

wherein

M is sodium, potassium, or lithium;

$R_1$ is $C_1$-$C_6$ alkyl; and $R_2$ is $CF_2H$, $CFH_2$, $CF_3$, $CCl_2H$, $CClH_2$, or $CCl_3$.

2. The process of claim 1, further comprising coupling the compound of Formula VI with a trialkyl orthoformate to provide a compound of Formula VII

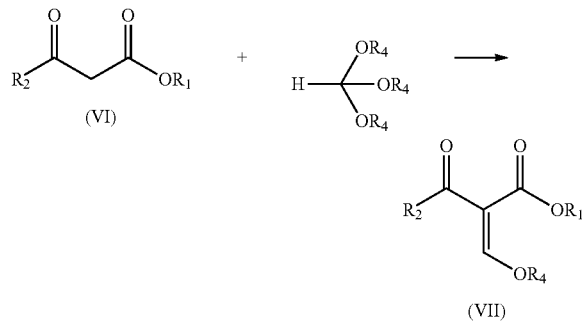

(VI)

(VII)

wherein $R_4$ is $C_1$-$C_6$ alkyl.

3. The process of claim 2, additionally comprising reacting the compound of Formula VII with methyl hydrazine hydrate ($H_3CNHNH_2 \cdot H_2O$) or methyl hydrazine to provide a compound of Formula I

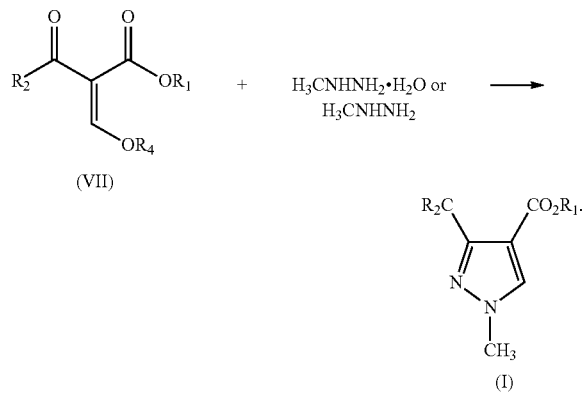

(VII)

(I)

4. The process of claim 3, wherein the compound of Formula V is prepared by reacting a haloalkylacetate of Formula III with an alkyl acetate of Formula IV to provide the enolate salt of Formula V

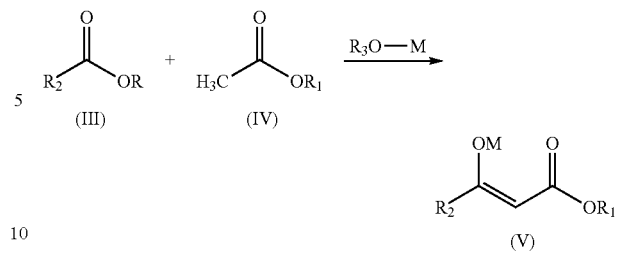

(III)   (IV)

(V)

wherein

R is $C_1$-$C_6$ alkyl; and $R_3$ is methyl or ethyl.

5. The process of claim 1, wherein the carbon dioxide is added to the water as gaseous carbon dioxide or solid carbon dioxide (dry ice) and thereby generates carbonic acid in situ.

6. The process of claim 3, wherein the compound of Formula I is purified in situ by precipitation from a solvent mixture.

7. The process of claim 5, wherein the solvent mixture is selected from the group consisting of toluene/petroleum ether, toluene/hexane, toluene/pentane, toluene/heptane, toluene/cyclohexane, toluene/ethyl acetate, toluene/isopropylacetate, and toluene/butyl acetate.

8. The process of claim 7, wherein the pressure of carbon dioxide is from about 0.1 kg/cm² to about 5 kg/cm².

9. The process of claim 3, wherein the reaction of Formula VII with methyl hydrazine hydrate ($H_3CNHNH_2 \cdot H_2O$) or methyl hydrazine is conducted in the presence of a weak base.

10. The process of claim 9, wherein the weak base is selected from a carbonate salt or a bicarbonate salt or a combination thereof.

11. The process of claim 10, wherein the carbonate salt is $Na_2CO_3$, $K_2CO_3$, $Li_2CO_3$, $CaCO_3$, or $MgCO_3$ or a combination of any of the foregoing.

12. The process of claim 10, the bicarbonate salt is of $NaHCO_3$, $KHCO_3$, or $LiHCO_3$, or a combination of any of the foregoing.

13. The process of claim 9 wherein the reaction of Formula VII with methyl hydrazine hydrate ($H_3CNHNH_2 \cdot H_2O$) or methyl hydrazine is conducted in a two Phase solution consisting of water and a water-immiscible organic solvent.

14. The process of claim 13, wherein the water-immiscible organic solvent is toluene, xylene, pentane, hexane, heptane, cyclohexane, or methyl tertiary butyl ethyl (MTBE), or a combination of any of the foregoing.

15. The process of claim 9, wherein the reaction of Formula VII with methyl hydrazine hydrate ($H_3CNHNH_2 \cdot H_2O$) or methyl hydrazine is conducted at a temperature of from about −10° C. to about 10° C.

16. The process of claim 3, wherein
$R_1$ is ethyl, $R_2$ is $CF_2H$ or $CF_3$, $R_3$ is ethyl, M is sodium, and $R_4$ is ethyl.

17. The process of claim 4, wherein
R is ethyl or methyl, $R_2$ is $CF_2H$ or $CF_3$, $R_3$ is ethyl, M is sodium, and $R_4$ is ethyl.

* * * * *